United States Patent [19]

Teasdale

[11] Patent Number: 5,759,821
[45] Date of Patent: Jun. 2, 1998

[54] METHOD OF RANDOM AMPLIFICATION OF POLYMORPHIC DNA

[75] Inventor: Robert D. Teasdale, Robina, Australia

[73] Assignee: F B Investments Pty Ltd., Woolloongabba, Australia

[21] Appl. No.: 537,730

[22] PCT Filed: Apr. 18, 1994

[86] PCT No.: PCT/AU94/00197

§ 371 Date: Dec. 28, 1995

§ 102(e) Date: Dec. 28, 1995

[87] PCT Pub. No.: WO94/24307

PCT Pub. Date: Oct. 27, 1994

[30] Foreign Application Priority Data

Apr. 16, 1993 [AU] Australia .................. PL8331
Jun. 1, 1993 [AU] Australia .................. PL9142

[51] Int. Cl.$^6$ .................. C12P 19/34; C07H 21/04
[52] U.S. Cl. .................. 435/91.2; 536/24.3
[58] Field of Search .................. 435/6, 91.2, 172.1, 435/91.1; 536/24.3

[56] References Cited

U.S. PATENT DOCUMENTS 5,126,239  6/1992  Livak et al. .................. 435/6
5,437,697  8/1995  Sebastian et al. .................. 47/58

FOREIGN PATENT DOCUMENTS

B-77820/91  10/1991  Australia .
0412005  6/1991  European Pat. Off. ........ C12N 15/82
0436467  10/1991  European Pat. Off. ........ C12N 15/29

OTHER PUBLICATIONS

Welsh and McClelland (1990) Nucleic Acids Res. 18:7213–18.
Caetano–Anolles et al. (1991) BioTechnology 9: 553–7.
Williams et al. (1990) Nucleic Acids Res. 18:6531–35.
Zhang et al. (1991) BioTechniques 11:60.
Reiter et al. PNAS (1992) 89:1477–81.

Biological Abstracts, vol. 79, 1985, Philadelphia, PA., U.S.; Abstract No. 30608, Ross, S.D., et al., "Gibberellin A4/7 and the promotion of flowering in Pinus radiata: Effects on partitioning of photoassimilate within the bud during primordia differentiation".
Biological Abstracts, vol. 95, 1993, Philadelphia, Pennsylvania, U.S.; Abstract No. 15786, Cremer, K. W., "Relations between reproductive growth and vegetative growth of Pinus–radiata".

*Primary Examiner*—W. Gary Jones
*Assistant Examiner*—Amy Atzel
*Attorney, Agent, or Firm*—Dvorak & Orum

[57] ABSTRACT

Methods of random amplification of polymorphic DNA are provided which comprise the use of concentrations of nucleotide triphosphate reagents at concentrations of from 0.4 to 0.6 mM. Magnesium is also used according to:

$$[Mg]=[ATP]+[GTP]+[TTP]+[CTP]+1.5\pm0.3 \text{ mM}$$

pH is controlled by Tris HCL at 10 mM and KCl at 50 mM with a pH of 8.8 to 9.0. Heat resistant polymerase enzyme is used at a concentration of 0.7 units per 13.5 µl reaction volume. The concentration of oligonucleotide primers is selected to be from 0.4 to 0.8 µM. When more than one oligonucleotide primer is used a stoichiometry of from 1:1.25 to 1:0.8 is used. Mathematical modeling is used to describe the distribution of numbers of polymorphisms produce per primer, combined Poisson and binomial distributions are used to describe the frequency distribution of polymorphisms over a number of different primer molecules, and the fraction of primers mean value ($F_m$) that are preselected for use in a pre-screening regime is selected by the expression $$F_m = \int\limits_{H\mu \to 0} (N_s/(2N_m))$$

where $N_m$ is the number of individuals in the population used for linkage analysis, $N_s$ is the number of individuals in the pre-screening, H is the observed heterozygosity of the pedigree under study, and µ is the mean number of bands per reaction.

18 Claims, No Drawings

METHOD OF RANDOM AMPLIFICATION OF POLYMORPHIC DNA

This invention relates to improvements to methods of random amplification of polymorphic DNA.

This invention has particular but not exclusive application to methods of random amplification of polymorphic DNA for production of molecular markers for genetic studies such as production of genetic maps and for development of correlations between map markers and valuable traits in genetic improvement of plants and animals, and for illustrative purposes reference will be made to such application. However, it is to be understood that this invention could be used in other applications apparent to those skilled in the art.

The method of Random Amplification of Polymorphic DNA (RAPD), an application of the Polymerase Chain Reaction (PCR) method (Mullis et al. 1987), to produce molecular markers for genetic studies is known. These procedures dramatically extend and improve the productivity and reliability of the RAPD method, providing much more information than that obtainable with preceding methods. The RAPD method involves the use of an oligonucleotide of arbitrary short sequence, generally 10 bases long, as a primer in the Polymerase Chain Reaction. This oligonucleotide primer will bind to numerous complementary sites which occur randomly in the DNA of the genome under study. Where two such sites are suitably juxtapositioned on opposite chains, the intervening sequences will be copied in each direction, concomitantly also producing new binding sites, so that in each cycle of the PCR process doubling of these sequences occurs.

In principle, the quantity of DNA increases exponentially from as little as a single molecule up to several μg over repeated cycles in the PCR process. These products from various sites will generally be of different length and are usually separated by electrophoresis through an agarose gel, then detected as discreet bands by fluorescence emission following ethidium bromide staining and excitation with ultra violet light. Alternative separation and detection methods may also be used, such as polyacrylamide gel electrophoresis and silver staining. Typically 2 to 10 bands (products) can be detected which are from independent sites randomly dispersed across the genome.

The total product yield in a PCR reaction is limited, presumably by primer limitation and/or product (pyrophosphate) inhibition, so that high efficiency in production from one (or a few) more effective sites will lead to reaction termination before some potentially valuable products reach detectable levels, so that these potential products are competitively displaced from detection. Use of a number of oligonucleotides of specific sequence will each yield a characteristic set of bands from a particular set of sites randomly dispersed over the genome. Genetic changes at particular sites will lead to loss of some DNA products, changes in size, or generation of new products, which can be scored as genetic polymorphisms and can be used as genetic markers (molecular markers). The number of different oligonucleotide primers 10 bases in length is $4^{10}=1048576$, of which ca 30% are of generally preferred GC content (50 to 80%) so that the method provides approximately 300,000 possible primers, which is an effectively unlimited number for testing.

Relevant disclosures indicating the state of the art are as follows:

Williams, J. G. K., A. R. Kubelik, K. J. Livak, J. A. Rafalski & S. V. Tingey (1990) DNA polymorphisms amplified by arbitrary primers are useful as genetic markers. Nucleic Acids Research 18(22): 6531–6535.

Reiter, R. S., J. G. K. Williams, K. A. Feldman, J. A. Rafalski, S. V. Tingey & P. A. Scolnik (1992) Global and local genome mapping in Arabidopsis thaliana by using recombinant inbred lines and random amplified polymorphic DNAs. Proceedings National Academy of Science U.S.A. 89: 1477–1481.

Martin, G. B., J. G. K. Williams & S. D. Tanksley (1991) Rapid identification of markers linked to a Pseudomonas resistance gene in tomato using random markers and near-isogenic lines. Proceedings National Academy of Science U.S.A. 88: 2236–2340.

Livak, K. J., J. A. Rafalski, S. V. Tingey and J. G. Williams. Process for detecting polymorphisms on the basis of nucleotide differences. U.S. Pat. No. 5,126,239. 30 Jun. 1992. Assignee: E. I. Du Pont de Nemours and Company. Wilmington, Del., U.S.A.

Mullis, K. B., H. A. Ehrlich, N. Arnheim, R. K. Saiki and S. J. Scharf. Process for amplifying, detecting and/or cloning nucleic acid sequences. U.S. Pat. No. 4,683,195. 28 Jul. 1987. Assignee: Cetus Corporation, Emeryville, Calif., U.S.A.

The procedure is limited in its application by the number of bands which can be resolved in each relatively expensive reaction. Secondly, the process suffers from lack of reproducibility occurring with many bands. Thirdly, the process as currently performed has an inability to reliably use minimal quantities of DNA. Fourthly, the current methods need to use large numbers of expensive oligonucleotide primers to generate the numbers of polymorphic markers required. Finally, the current process exhibits a tendency for production of RAPD bands and other PCR products from multicopy sequences rather than those of low copy number.

The present invention aims to substantially alleviate at least some of the above disadvantages and to provide methods of random amplification of polymorphic DNA which will be reliable and efficient in use. Other objects and advantages of this invention will hereinafter become apparent.

With the foregoing and other objects in view, this invention in one aspect resides broadly in a method of random amplification of polymorphic DNA including the steps of:

providing one or more oligonucleotides of about 10 bases adapted to bind to complementary sites which occur randomly in the DNA of a genome, and using said oligo nucleotide(s) as a primer in a plurality of passages of a polymerase chain reaction, wherein the four nucleotide triphosphate reagents Adenosine triphosphate (ATP), Guanosine triphosphate (GTP), Cytosine triphosphate (CTP), and Thymidine triphosphate (TTP) are each employed in the reactions at a concentration of at least 0.4 mM.

The use of such very high levels of each of the four nucleotide triphosphates Adenosine triphosphate (ATP), Guanosine triphosphate (GTP), Cytosine triphosphate (CTP), and Thymidine triphosphate (TTP) flies in the face of conventional wisdom, it being generally regarded that such concentrations lead to a lack of specificity. The coupling of the present method with protocols described hereinafter allows the use of high concentrations with improved levels of information being determinable from each reaction. Preferably, the nucleotide triphosphates are utilized in approximately equal concentrations in the range of 0.4 to 0.6 mM. The level of magnesium is preferably correspondingly high during the PCR reactions employed for production of RAPD markers such that:

$$[Mg]=[ATP]+[GTP]+[TTP]+[CTP]+1.5\pm0.3\ mM$$

Other reaction conditions are standard to those skilled in the art and typically include a buffer to control pH in the vicinity of 8.8 (the preferred buffer consists of Tris HCL at 10 mM and KCl at 50 mM with a ph of 8.8 to 9.0), a heat resistant polymerase enzyme, specifically the Perkin Elmer Cetus Taq polymerase (or equivalent) at a concentration of 0.7 units per 13.5 µl reaction volume.

Preferably, the concentration of each of the oligonucleotide primers for optimal reproducibility should be in the range 0.4 to 0.8 µM, which is generally above that used in RAPD and other PCR reactions. Moreover, when more than one oligonucleotide primer is used in a single reaction, these should be kept in a stoichiometry close to 1:1 (range 1:1.25 to 1:0.8). Other thermal cycling conditions are within the range known to those skilled in the art, typically consisting of 3 cycles with denaturation for 60 second at 94° C., annealing at 36° C. for 60 seconds, and extension at 72° C. for 120 seconds. Typically, a further 47 cycles are carried out at an identical temperature but with the period of denaturation at 94° C. reduced to only 15 seconds, annealing for 1 second, and extension for 90 seconds.

Preferably, the genomic DNA is processed by shearing or other technique, be it physical, chemical or enzymatic, to cleave genomic DNA at specific or non-specific sites, for the purpose of increasing effectiveness of oligonucleotide primers to generate products from complementary sequences for PCR reactions in general, and RAPD reactions in particular, by diminishing the size of target DNA sequences to lengths closer to the minimum containing the sequence to be amplified.

In another aspect this invention resides in a method of cleaving genomic DNA to a minimum size containing a pair of binding sites and including heating said DNA to denaturation temperature, and cooling to promote cross strand annealing, wherein said DNA is heated at a concentration of at least 50 ng per microlitre. Preferably, the concentration of DNA is about 100 ng per microliter. The temperature of denaturation will generally be in the region of 90° to 94° C. and is preferably 90° C. and the DNA held at that temperature for about 5 minutes.

It has been observed by the present applicant that production of many random PCR products is affected by the concentration of genomic DNA used, with bands both appearing and disappearing as the concentration is lowered. This can lead to homozygous bands being incorrectly scored as polymorphic, false negative scores being assigned to some truly polymorphic bands (with apparent segregation distortion), or the marker being rejected as too unreliable for use. The present applicant has determined that a major cause of the failure to produce many RAPD markers in a reliable manner is that the various positions along the genomic DNA (that are potential sites for initiation of randomly-primed PCR reactions) do not behave equivalently, with many sites behaving with markedly reduced effectiveness.

The effectiveness of sites is affected by competition between the binding of primers to sites on the genomic DNA and the self-annealing of this DNA with its complementary strand.

Estimates from theoretical models indicate that self-annealing increases massively (non linearly) with molecular weight of the DNA so that a considerable competitive inequality occurs which particularly disadvantages sites in longer DNA molecules. The effect of this re-annealing is approximately described by the expression, $$[P.DNA]=[P]\{\sqrt{(k^2[P]^2+4k[DNA])}-k[P]\}/2 \; k^{-1})$$

where [P.DNA] is the concentration of primer-bound template DNA species for initiation of the RAPD-type band, k is the association constant for the initial primer binding to genomic DNA, and f is the ratio of the total length of the genomic strand bearing the site for amplification to the length of the primer species. A maximum in [P.DNA] will lead to a maximum in product yield from this site. It is noted that, for increase in f, the denominator will increase very much more significantly than will the numerator; the effect of increasing f by factors of say 1.5 to 10 (which are considered realistic) is therefore a very considerable decrease in [P.DNA].

The re-annealing tendency can be diminished, in accordance with the above equation, by increasing the concentration of primer (increase in [P]), and shortening the length of the genomic DNA chains. By making the genomic DNA a more effective template in this way, PCR products in these reactions will be more reliable, with lower requirement for genomic DNA sample and less susceptibility to exogenous contamination.

The optimum level of each primer for band reproducibility has been determined as ca. 0.4 µM which is in considerable excess of that consumed in the reaction (the amount of final reaction product in PCR is also determined by factors additional to primer concentration so that a plateau is generally obtained). This level of primer significantly exceeds that generally employed for this procedure in the simplest case of a single primer, with the increase over standard conditions yet greater when two more primers are used in combination. Higher concentrations of primer sometimes generate a smear of additional products so that the concentration of ca. 0.4 µM is often the practical optimum. For those reactions where reproducibility of bands is not a problem, optimum resolution may sometimes be obtained at lower concentrations of primer.

Reduction in the molecular weight of the template DNA will lead to reduction in tendency to re-anneal. A significant improvement to the standard RAPD procedure is therefore obtained through the controlled reduction in molecular weight of the genomic DNA to the minimum size containing the pair of primer binding sites. However, if the degree of size reduction varies from preparation to preparation, there will be differences in product profile that do not reflect genetic differences.

Molecular weight reduction can be effected by heating relatively concentrated DNA solutions to denaturing temperatures, then cooling, whereupon cross-strand annealing occurs which results in strand breakage as the DNA helices rewind. The frequency of strand breakage increases with increasing DNA concentration, so that fixed conditions can provide reasonably consistent reduction in molecular weight. Alternative methods such as mechanical shearing by repeated aspirating through a syringe needle are also effective. Random reduction in the molecular weight of DNA can lead to breakage between two primer-binding sites so that potential RAPD product loss occurs. The probability of this occurring increases with size of the RAPD band and with the extent of breakage of the template DNA strands. However, the practical significance of this has been determined by modelling and, for example, the effect of reducing the weight-average size of template DNA down to 5000 base pairs (normally distributed) shown to be insignificant with RAPD bands up to 3000 base pairs in length; it is preferable to make the final mean size approximately twice the size of the largest PCR product to be assessed. Any method of size reduction for the specific purpose of improving the reliability of the RAPD procedure is covered by this invention.

Practical control of average template DNA size from sample to sample can be difficult and the tendency for self-annealing may still significantly effect the reproducibility of RAPD reactions. Such variability can generally be determined by varying the concentration of DNA template with a selected test primer that produces a large number of PCR bands, using template DNA concentrations that bracket the final concentration used in the RAPD reaction (preferred test range for Pinus spp. is ca. 50 genomes to 300 genomes per 13.5 μl reaction volume) by a factor of at least two. Accordingly, different DNA preparations from a target genotype (or alternative genotypes in some cases) are therefore trialled in such a dilution study and only those showing no differences in product profiles used in subsequent RAPD reactions.

Other reaction conditions have also been optimised to provide the maximum number of resolvable products. The concentrations of nucleotide triphosphates were increased to ca. 0.5 mM in each, which is ca. four fold higher than the concentrations generally used and recommended in the original RAPD procedure (williams et al. 1990). The concentration of magnesium was correspondingly increased to 3.5 mM, which is also much greater than is generally used in other RAPD and PCR reaction conditions. Other conditions were in accordance with typical procedure for RAPD reactions (as known to those skilled in the art) including buffer (10 mM TrisHCl, 50 mM KCl, pH 8.8) and Taq polymerase (0.7 units/13.5μl reaction).

The temperature conditions for thermal cycling were modified to minimise the time at high temperature so as to preserve activity of the heat resistance polymerase during thermal cycling, thereby providing maximum product yield with efficient use of polymerase enzyme. These PCR conditions involve an initial three cycles with denaturation for 1 minute at 94° C., 1 minute annealing at 36° C., and 2 minutes extension at 72° C., using the fastest possible transition rates between phases; a further 47 cycles are carried out with identical temperatures but reduced cycle times— denaturation for 15 seconds, annealing for 1 second, and extension for 90 seconds. These conditions are appropriate for a Perkin Elmer Cetus 480 thermal cycler using standard 0.5 ml reaction tubes, but may vary slightly with alternative instruments and tubes of different wall thickness. Reaction products are analyzed using standard methods, preferably by electrophoresis through agarose gel (1.4%) containing ethidium bromide (0.05%) and detection of bands by fluorescence at 590 nm upon excitation with ultraviolet light.

The PCR procedure with arbitrary primers is strongly biased to detection of multi-copy genes. Polymorphisms occurring in such multi-copy genes will sometimes be masked by products from alternative loci, or will appear as changes in product yield (band intensity) which are less-reliable as markers than discreet polymorphisms. Where RAPD markers are obtained from multi-copy genes, they are less suitable for some subsequent applications, such as in identification of corresponding cloned fragments of genomic DNA. It has been reported (Reiter et al. 1992) that for Arabidopsis thaliana, only ca. 50% of RAPD fragments assessed are from sequences represented by three or less copies per genome. The shearing of genomic DNA combined with the improved reaction conditions increases the probability that a detectable product will be derived from a gene of single or low copy number, so that the methods described in the present invention will generally yield more valuable markers than standard RAPD methods.

A procedure and formula has been developed by the applicant to markedly improve the cost effectiveness of mapping using such procedures through optimal use of multiple polymorphisms per assay. It has been shown that the number of PCR products generated by reaction of an arbitrarily selected primer is random and approximately described by a Poisson distribution about the mean number of bands per reaction (μ). Furthermore, within a set of reactions all having the same number of total bands generated from different primers, the number of polymorphisms can be approximately described by a binomial distribution. It has therefore been calculated that the probability ($S_n$) with which any particular number of polymorphisms per primer will be obtained is approximately described by the expression.

$$S_n = \frac{(H\mu)^n}{n!} \cdot e^{-H\mu} \tag{6}$$

Where H is the observed heterozygosity of the pedigree under study, that is the probability that any band (PCR product) selected at random will be polymorphic. Such distributions allow estimation of the numbers of primers which will provide 1, 2, 3, 4, 5, etc respective markers per reaction. The product Hμ is recognised to correspond to the average number of polymorphisms per primer, which may be easily estimated with a small number of reactions.

Of principal interest for efficiency estimations is determination of the number of polymorphisms when only those reactions are selected which meet a threshold in number of polymorphisms per reaction. The probable number of polymorphisms (Tn) above a threshold $n_t$ is described by the equation (7) below.

$$T_n = H\mu - H\mu \cdot e^{-H\mu} \cdot \left\{ 1 + \frac{H\mu}{1} + \frac{(H\mu)^2}{2!} + \frac{(H\mu)^3}{3!} + \ldots + \frac{(H\mu)^{n_t-2}}{(n_t-2)!} \right\} \tag{7}$$

Equation (7) provides a basis for modelling the effect of pre-screening primers. With a relatively small sample, the impact of selected threshold values on the efficiency of the process can be determined, that is, there can be minimisation of the total number of reactions to generate the target number of markers and corresponding genotype assessments on the mapping population.

For example, if an average of 16 bands are produced per primer (μ=16) and with heterozygosity given by q=0.05, then the probability of an arbitrarily selected primer yielding one polymorphic band in a reaction is estimated to be $P_1$=0.36, so that the screening of 200 randomly selected primers will likely yield 72 that produce a single polymorphic product; the corresponding probabilities for 2, 3 and 4 markers per primer are: $P_2$=0.14, $P_3$=0.04, and $P_4$=0.008, with 0.449 (44.9%) of primers yielding no markers. Estimation of the most appropriate threshold will depend upon the respective numbers of genotypes in the mapping ($N_m$) and pre-screening ($N_s$) phases. For example, pre-screening may involve use of DNA from 3 genotypes (such as from each parent and the F1 progeny in a pedigree) and mapping with DNA from a set of 96 progeny. In general, the number of reactions will be described by equation (8) where $N_m$ is the number of individuals in the population used for linkage analysis, $N_s$ is the number of individuals in the pre-screening—which can include an equivalent measure of the cost of primers to be screened in "reaction equivalents". Cost effectiveness will therefore be optimised by minimising the number of "reaction equivalents", or reactions per linked marker ($R_n$) to attain the linkage information finally required.

$$R_n(N_m+N_s \cdot F_n)/T_n \tag{8}$$

where $F_n$ is the fraction of primers selected to yield at least $n_t$ polymorphisms per primer, and $T_n$ is the probable number of polymorphisms these selected primers provide. $F_n$ is approximately given by equation 9 as follows.

$$F_n = 1 - e^{-H\mu}\left(\sum_{0}^{n-1} \frac{(H\mu)^n}{n!}\right) \tag{9}$$

The effect of pre-screening is illustrated by modelling values of $R_n$ for a typical experimental system. Pre-screening involves RAPD reactions of candidate primers with DNA from two parents and the F1 so that, with the cost of each primer assumed to be approximately equal to the consumable costs of two RAPD reactions, $N_s=5$. Linkage analysis is determined with 96 individuals, corresponding to 92 haplotypes and four F1 samples used for reference, so that $N_m=96$ (which corresponds to a simple multiple of the capacity of most thermocyclers). It is calculated for this particular example that, when the minimum thresholds ($n_t$) are one, two, three and four markers per primer, there are 72, 53, 62 and 155 reactions per marker respectively.

The optimum of R=53 is therefore obtained by using only those primers producing one marker per reaction. In the present example approximately 19% of the primers assessed will meet this requirement, and the final average number of markers per primer is ca. 2.30, so that to obtain a set of, say, 300 markers, ca. 685 candidate primers will need to be pre-screened to provide 130 suitable primers, requiring ca. 15,900 successful reactions. Without such pre-screening ca. 52,000 reactions would be involved, and with selection of all primers producing at least one polymorphism, ca. 21,690 reactions would be needed for the same mapping information (assuming conditions constant to provide the same $\mu=16$ and H=0.05 values).

The variation in $F_n$, the optimum fraction of primers selected through pre-screening to meet specific $n_t$ values, with increase in Hμ was examined using these equations. This revealed that the fraction of primers ($F_n$) providing lowest $R_n$ values is confined to a reasonably narrow band, in the example of the $N_s=5$ and $N_m=96$ values of the above example, a range of 4 to 20% of the candidate primers is obtained. This range of Hμ and the particular $n_t$ values at which transitions occur will vary with the particular selection regime, ie the ratio $N_s/N_m$.

With transition from one threshold $n_{t-1}$ to the next $n_t$ with increase in μH, the fraction of primers that meet the requirement for optimal efficiency can be calculated using equations (8) and (9), with recognition that at each transition $R_{n-1}=R_n$. It follows that this transition must occur at the point where, $$\frac{N_s}{N_m} = \frac{T_n}{(n_t - 1)} - F_n \tag{10}$$

Equation (10) may be solved with various $n_t$ values to obtain the Hμ value at which such thresholds are appropriate. At $n_t=2$, the solution is provided by the Hμ value satisfying equation (11).

$$(N_s/N_m) = H\mu - 1 + e^{-H\mu} \tag{11}$$

This may be readily solved graphically, numerically, or with use of the standard series expansion of $e^{-H\mu}$. In general, the value of Hμ at which transition to the next higher $n_t$ value is appropriate for optimal efficiency can be approximately related to $(N_s/N_m)$ by, $$(n_t - 1)(N_s/N_m) = (H\mu)^{n_t}/n_t! \tag{12}$$

Accordingly, for $N_s/N_m=5/96$, equation (12) indicates a Hμ value of 0.33 will lead to selection of only those primers providing more than two polymorphisms per primer reaction, which is close to the precise value of 0.342 obtained with accurate solution of equation (11).

Thus, the optimum sets of values correspond to a relatively constant fraction of the number of primers employed, with this range narrowing for higher Hμ values, and the mean increasing gently. At any point of transition from one $n_t$ to the next at the same Hμ value, the mean value ($F_m$) for the fraction of primers that are preselected is given by $F_m=(F_n+F_{n-1})/2$, which from equation (9) is readily shown to be the monotonically increasing series, $$F_m = e^{-H\mu}\left(\sum_{0}^{n-1} \frac{(-H\mu)^n}{n!} \cdot (n-2)\right)/2 \tag{13}$$

When combined with equation (12) to provide optimal efficiency, the limit value is found to be, $$\frac{F_m}{H\mu \to 0} \approx \sqrt{(N_s/(2N_m))} \tag{14}$$

As the fraction of primers to be used does not increase markedly over large increases in Hμ, equation (14) provides a simple means to determine the fraction of primers to be used for maximum efficiency in any practical screening program. With recognition that in applying a pre-screening ratio the effective value of this ratio should also reflect use of selected primers in any additional genotyping and screening activities, which could increase the $N_m$ value considerably. For example, with the not-unrealistic value of 500 for $N_m$, which provides the corresponding value of $N_s/N_m=1/100$, the fraction of primers to be used is approximately estimated from equation (15) as $F_m \approx \sqrt{(5/(2\times 500))}=0.07$. If (say) 100 markers are required, then for this pre-screen system it will be necessary to select only the top 7% of primers, irrespective of the value of Hμ, until sufficient are obtained to yield 100 markers. Thus, the numbers of markers required will be dictated by genome size and marker density requirements; and the Ns/Nm ratio will dictate which fraction of primers should be selected through pre-screening—with the number of candidate primers to be screened adjusted according to heterozygosity and average number of bands per reaction.

The above examples are indicative of only one data gathering system and alternative arrangements may differ significantly in specific details. Nevertheless, pre-screening of primers will generally provide advantages in efficiency, and in many instances these will be of considerable significance.

It will of course be realised that while the above has been given by way of illustrative example of this invention, all such and other modifications and variations thereto as would be apparent to persons skilled in the art are deemed to fall within the broad scope and ambit of this invention as defined in the claims appended hereto.

I claim:

1. A method of selecting primers for use in random amplification of polymorphic DNA (RAPD) comprising the steps of:

A. providing a population of organisms;
   B. selecting a subset of said population which comprises individuals of the population, and isolating genomic DNA from each of the individuals;
   C. providing a plurality of oligonucleotides of about 10 bases which bind to complementary sites occurring randomly in the genomic DNA of said organisms;
   D. amplifying the isolated genomic DNA from each individual of the population subset employing said oligonucleotides as primers;

E. detecting polymorphisms in the genomic DNA of the population subset;

F. ranking the oligonucleotide primers according to the number of detectable polymorphisms exhibited utilizing each primer, wherein the primers are ranked in descending order with primers detecting the most polymorphisms ranked first, and primers not detecting any polymorphisms ranked last;

G. calculating $F_m$, wherein $F_m$ is a fraction of primers to be subsequently used to amplify genomic DNA of the entire population, wherein $F_m$ is calculated using the formula $$F_m = \sqrt{(N_s/(2N_m))}$$

$N_s$ is the number of individuals in the population subset, and $N_m$ is the number of individuals in the entire population;

H. selecting primers starting at the top of the ranking and following in descending order until a fraction of primers is obtained equivalent to the numerical value of $F_m$, wherein the primers selected are a fraction of the total primers used in step D that generate useful polymorphism information in RAPD reactions for the entire population of organisms.

2. The method according to claim 1, further comprising four nucleotide triphosphate reagents, Adenosine triphosphate (ATP), Guanosine triphosphate (GTP), Cytosine triphosphate (CTP), and Thymidine triphosphate (TTP), each employed in the amplification step at a concentration of at least 0.4 mM.

3. The method according to claim 2, wherein said concentrations of each of the four nucleotide triphosphates are substantially equal and in the range of 0.4 to 0.6 mM.

4. The method according to claim 1, further comprising magnesium in the amplification step, in a concentration such that:

$$[Mg] = [ATP] + [GTP] + [TTP] + [CTP] + 1.5 \pm 0.3 \text{ mM}.$$

5. The method according to claim 4, wherein the amplification step occurs at a pH of approximately 8.8.

6. The method according to claim 5, wherein the pH is adjusted utilizing a buffer consisting of Tris HCL at 10 mM and KCL at 50 mM, to obtain a pH in the range of 8.8 to 9.0.

7. The method according to claim 1, further comprising a heat resistant polymerase enzyme selected from Perkin Elmer Cetus Taq polymerase or equivalent, at a concentration of approximately 0.7 units per 13.5 µl.

8. The method according to claim 1, wherein the concentration of each oligonucleotide primer is in the range of 0.4 to 0.8 µM, and wherein a concentration of multiple primers is in a stoichiometry in a range of 1:1.25 to 1:0.8.

9. The method according to claim 1, wherein the amplification step further comprises 3 cycles, including denaturation at 94° C. for 60 seconds, annealing at 36° C. for 60 seconds, and extension at 72° C. for 120 seconds, and further comprises 47 cycles of denaturation at 94° C. for 15 seconds, annealing at 36° C. for 1 second, and extension at 72° C. for 90 seconds.

10. The method according to claim 1, wherein the genomic DNA is cleaved by physical, chemical, or enzymatic means at specific or non-specific sites, before performing the amplification step.

11. The method according to claim 2, further comprising magnesium in the amplification step, in a concentration such that:

$$[Mg] = [ATP] + [GTP] + [TTP] + [CTP] + 1.5 \pm 0.3 \text{ mM}.$$

12. The method according to claim 3, further comprising magnesium in the amplification step, in a concentration such that:

$$[Mg] = [ATP] + [GTP] + [TTP] + [CTP] + 1.5 \pm 0.3 \text{ mM}.$$

13. The method according to claim 2, further comprising a heat resistant polymerase enzyme selected from Perkin Elmer Cetus Taq polymerase or equivalent, at a concentration of approximately 0.7 units per 13.5 µl.

14. The method according to claim 3, further comprising a heat resistant polymerase enzyme selected from Perkin Elmer Cetus Taq polymerase or equivalent, at a concentration of approximately 0.7 units per 13.5 µl.

15. The method according to claim 4, further comprising a heat resistant polymerase enzyme selected from Perkin Elmer Cetus Taq polymerase or equivalent, at a concentration of approximately 0.7 units per 13.5 µl.

16. The method according to claim 5, further comprising a heat resistant polymerase enzyme selected from Perkin Elmer Cetus Taq polymerase or equivalent, at a concentration of approximately 0.7 units per 13.5 µl.

17. The method according to claim 10, further comprising an amplification step for each individual of the entire population of organisms, and wherein the fraction of total primers is selected prior to performing the amplification steps for the entire population of organisms.

18. The method according to claim 10, wherein combined Poisson and binomial distributions are used to describe a frequency distribution of polymorphisms over a number of different primers.

* * * * *